United States Patent
O'Donoghue et al.

(10) Patent No.: US 11,561,218 B2
(45) Date of Patent: Jan. 24, 2023

(54) METHOD FOR DETECTING A DENGUE INFECTION

(71) Applicant: Siemens Healthcare Diagnostics Inc., Tarrytown, NY (US)

(72) Inventors: Kieran O'Donoghue, Dundalk (IE); Rory Sobolewski, Laytown (IE)

(73) Assignee: Siemens Healthcare Diagnostics he., Tarrytown, NY (US)

(*) Notice: Subject to any disclaimer, the term of this patent is extended or adjusted under 35 U.S.C. 154(b) by 947 days.

(21) Appl. No.: 16/297,531

(22) Filed: Mar. 8, 2019

(65) Prior Publication Data

US 2019/0277834 A1    Sep. 12, 2019

(30) Foreign Application Priority Data

Mar. 9, 2018    (EP) .................................... 18160915

(51) Int. Cl.
| | | |
|---|---|---|
| G01N 33/50 | (2006.01) | |
| G01N 15/14 | (2006.01) | |
| G01N 15/02 | (2006.01) | |
| G01N 15/06 | (2006.01) | |
| G01N 15/00 | (2006.01) | |

(52) U.S. Cl.
CPC ..... *G01N 33/5094* (2013.01); *G01N 15/0205* (2013.01); *G01N 15/06* (2013.01); *G01N 15/14* (2013.01); *G01N 2015/0065* (2013.01); *G01N 2015/0084* (2013.01); *G01N 2015/0693* (2013.01); *G01N 2800/26* (2013.01)

(58) Field of Classification Search
CPC ........... G01N 33/5094; G01N 15/0205; G01N 15/06; G01N 15/14; G01N 2015/0065; G01N 2015/0084; G01N 2015/0693; G01N 2800/26; C12M 41/36; C12Q 1/06; C12Q 1/28; C12Q 1/70
See application file for complete search history.

(56) References Cited

U.S. PATENT DOCUMENTS

| | | | |
|---|---|---|---|
| 6,025,201 A | 2/2000 | Zelmanovic et al. | |
| 2015/0056607 A1 | 2/2015 | Jooris et al. | |
| 2015/0160240 A1* | 6/2015 | Abraham | G01N 33/573 |
| | | | 506/7 |

FOREIGN PATENT DOCUMENTS

| | | |
|---|---|---|
| CN | 104204767 A | 12/2014 |
| WO | WO2014186228 A1 | 11/2014 |

OTHER PUBLICATIONS

Simon-Lopez Ramon et al: "Monocyte Anisocytosis: a New Hematological Marker for the Detection of Dengue Fever"; Blood; The American Society of Hematology, vol. 116; Nov. 2010.

(Continued)

*Primary Examiner* — Samuel P Siefke
*Assistant Examiner* — Henry H Nguyen
(74) *Attorney, Agent, or Firm* — Dugan & Dugan, PC

(57) ABSTRACT

The invention relates to a method for detecting a dengue infection in a patient blood sample, comprising the steps: a) Performing an analysis of prespecified parameters of blood platelets and prespecified types of blood cells in the sample and determining parameter values for the prespecified parameters of the platelets and the prespecified types of cells; b) Obtaining sample parameters from the values determined in step a); and c) Evaluating the sample parameters in relation to a prespecified criterion, wherein, if the criterion is fulfilled, a dengue infection is present.

8 Claims, 4 Drawing Sheets

(56) References Cited

OTHER PUBLICATIONS

Scoffin Katriona: "Hematology Analyzers From Complete Blood Counts to Cell Morphology", Labcompare, May 23, 2014.
Database Medline [Online]; US National Library of Medicine (NLM), Bethesda, MD. US; Jan. 2012 (Jan. 2012); Jameel Tahir et al: "Changing Technical Fields hematological parameters in dengue viral infections."; Database accession No. NLM23855G82 abstract & Journal of Avus Medical College; Abbottabad : JAMC,vol. 24, No. 1, pp. 3-6, ISSN: 1025-9589; (2012).
Muller David A. et al: "Clinical and Laboratory Diagnosis of Dengue Virus Infection". Journal of Infectious Diseases. JID; vol. 215 No. suppl. 2; pp. S89-S95; (2017).
Mehta R C: "Importance of complete blood count and peripheral smear examination in early diagnosis of dengue patients"; Journal of Infectious Diseases Letters; vol. 2; No. 1; pp. 22-24 (2013).
Brasier Allan R. et al: "A Three-Component Biomarker Panel for Prediction of Dengue Hemorrhagic Fever"; American Journal of Tropical Medicine & Hygiene; vol. 86; No. 2; pp. 341-348 (2012).
Manas Kotepui et al: "Differentiating between dengue fever and malaria using hematological parameters in endemic areas of Thailand"; Infectious Diseases of Poverty vol. 6. No. 1; pp. 1-9 (2017).
European Search Report of European Application No. 18160915.7-1118 dated May 5, 2018.
Gibbs, G. et al.: "Abnormal ADVIA 2120i neutrophil cytogram in myelodysplastic syndrome"; International Journal of Laboratory Hematology; vol. 39; No. 3; Mar. 17, 2017; pp. 84-85.
Harris, N. et al.: "The ADVIA 2120 Hematology System: Flow Cytometry-Based Analysis of Blood and Body Fluids in the Routine Hematology Laboratory"; Laboratory Hematology; vol. 11, No. 1, Mar. 1, 2005; pp. 47-61.
Longanbach, S. et al.: "Automated blood cell analysis"; In: "Rodak's Hematology Clinical Principles and Applications Part III"; Jan. 1, 2016; Elsevier, St Louis; pp. 208-227.
Zhang W. et al.: "Reliability Evaluation of the Abnormal Alarm of ADVIA 2120i Hematology Analyzer", World Journal of Integrated Traditional and Western Medicine 2015, vol. 10, No. 6, year 2015.

\* cited by examiner

METHOD FOR DETECTING A DENGUE INFECTION

CROSS REFERENCE TO RELATED APPLICATION

This claims priority to European Patent Application No. EP 18160915.7, filed Mar. 9, 2018, which is hereby incorporated by reference herein in its entirety for all purposes.

FIELD

The invention relates to a method for detecting a dengue infection in a patient blood sample.

BACKGROUND

Dengue infections, such as dengue fever caused, for example, by the one of the distinct four dengue virus serotypes, DEN-1, DEN-2, DEN-3 and DEN-4, which belong to the genus *Flavivirus*, family Flaviviridae, are the cause of tens of millions of new infections worldwide per year. According to figures from the World Health Organization (WHO), the estimate of new infections per year ranges from 50 to 100 million people. Dengue is held to be endemic in over 100 countries. Almost half of the world's population is at risk to be infected. A dengue infection has the potential to become lethal if untreated.

The infection is mosquito-borne. The main vector that transmits the viruses that cause dengue is the *Aedes aegypti* mosquito. The viruses are passed on to humans through the bites of an infective female *Aedes* mosquito. The mosquito acquires the virus while feeding on the blood of an infected person.

Infected humans are the main carriers and multipliers of the virus as they serve as a source of the virus for uninfected mosquitoes. Typically, the virus circulates in the blood of an infected person for 2-7 days while the patient develops a fever. During this time, the infection can be transmitted via *Aedes* mosquitoes to other humans.

There are a number of methods available for the diagnosis of *plasmodium* infections. According to the Centers of Disease Control and Prevention (CDC) in the United States of America, the current methods for detecting the dengue virus include polymerase chain reaction (PCR) and real time (RT)-PCR, although assays are not commercially available for the latter. PCR operates on the principal that the virus genome sequence is known. A serum sample from the patient is combined with primers that will select for a section of the known sequence of the virus. If the virus is present, this known section of the DNA will be amplified to a detectable level.

Another known method are ELISA assays, which involve testing a serum sample from a patient for the presence of NS1, IgG, and/or IgM antibodies that appear in the blood serum 2-5 days post infection. However, false positives and cross reactions with other mosquito-borne viruses can obfuscate results.

Further, another method are PRNT assays, which are biological assays, based on the principal that specific virus serotypes become inactivated by a specific antibody, so it is no longer able to infect a cell culture. This is assessed by a reduction in plaques present. WHO guidelines exist, but as of yet, the method of performing PRNT is not standardized, leading to variability in the results.

Currently no dengue detection method exists that can be carried out as part of a standard blood cell count test.

SUMMARY

For automatic use, so-called automated cell counters are being employed with increasing success. Examples of such counters are the Advia 2120, Sysmex XE-2100 and also CellaVision DM96. These automated devices, apart from their high throughput rate, provide a number of benefits, such as, for example, higher objectivity (no observer-dependent variability), elimination of statistical variations which are usually associated with manual counting (counting high cell numbers), as well as the determination of numerous parameters which would not be available during manual counting and, as mentioned, a more efficient and cost-effective treatment. A few of these devices can process between 120 and 150 patient samples per hour.

The technical principles of the automatic single cell counting are based either on an impedance measurement or on an optical system (scattered light or absorption measurement).

With the impedance method, the counting of the cells and also the determination of their size is done on the basis of the detection and the measurement of changes in the electrical conductivity (impedance), which are caused by a particle which is moving through a small opening. Particles, such as blood cells, for example, are not themselves conductive, but are suspended in an electrically-conductive thinning medium. If such a suspension of cells is passed through an opening, during the passage of a single individual cell, the impedance of the electrical path between the two electrodes which are located on each side of the opening temporarily increases.

By contrast with the impedance methods, the optical method comprises the passing of a laser light beam through a thinned blood sample, which is detected in a continuous stream by the laser beam. Each cell which passes through the detection zone of the throughflow cells scatters the focused light. The scattered light is then detected by a photo detector and converted into an electrical impulse. The number of impulses generated here is directly proportional to the number of cells which pass through the detection zone within a specific period of time.

In the optical methods the light scattering of the individual cells which pass through the detection zone is measured at different angles. Information about cell structure, shape, and reflection ability is detected through this. These properties can be used to differentiate between different types of blood cells and use the derived parameters for diagnosis of deviations of the blood cells from the norm.

The values obtained by the two measurement methods are logically linked by means of differential diagnostics into a meaningful diagnosis result.

The sensitivity and specificity of diagnostic methods plays a major role within the framework of differential diagnostics, accordingly work on improving these properties is constantly being undertaken.

In terms of a gold standard, PCR has shown the highest success of correctly identifying the virus with a true positive rate (sensitivity) of approximately 80-90%. Success is thus not achieved to a sufficient extent with the conventional test methods in providing methods with high sensitivity and specificity, i.e., methods for detecting a dengue infection, which also recognize ill patients as such, as well as on the other hand being able to recognize a healthy patient as healthy.

The methods currently available for the detection of dengue virus all require specific assays and the isolation of blood serum in order to test for its presence in patient samples.

It is therefore an object of the present invention to provide a method for detecting a dengue infection in a blood sample which produces test results with higher sensitivity and specificity. It is a further object of the invention to provide a detection method for dengue infections which by the use of a number of independent parameters, allows a high specificity and sensitivity for dengue independently of other infections or different states of health of the patients. It is yet another object of the present invention to provide such a method which can be performed with the aid of automated blood analysis devices.

This object is inventively achieved by a method with the features claimed in claim 1.

The invention creates a method for detecting a dengue infection in a patient blood sample, comprising the steps a) Performing an analysis of prespecified parameters of blood platelets and prespecified types of blood cells in the sample and determining parameter values for the prespecified parameters of the platelets and the prespecified types of cells;

b) Obtaining sample parameters from the values determined in step a); and c) Evaluating the sample parameters in relation to a prespecified criterion, wherein, if the criterion is fulfilled, a dengue infection is present.

The patient blood sample examined in accordance with the invention as a rule involves a human blood sample. It is however also possible to examine blood samples of mammals.

A complete blood count (CBC) instrument operates by counting the types of cells present in whole blood as well as blood platelets, so there is no need to isolate serum to carry out the method according to the invention. The method for detecting a dengue infection is carried out based on elevated or decreased levels of certain types of cells and the number of platelets. As these cell and platelet counts are immediately available once the count is carried out, automated evaluation of the sample parameters according to the invention may then be employed to detect the presence of the dengue virus, at virtually no extra time, cost or expense.

From the measurement results obtained in step a) sample parameters are obtained and assessed in relation to a previously defined criterion, wherein a dengue infection is present if the criterion is fulfilled.

The term "prespecified criterion" as used herein relates to a criterion which was established on the basis of one or more sample parameters, in the case of the present invention especially based on cell volume parameters, cell number parameters and cell density parameters as well as the number of platelets. The criterion is determined on the basis of a comparison between infected blood samples and corresponding values of normal blood samples, for example, for the experimental investigations on which the present invention is based, a comparison of a number of dengue infected blood samples with corresponding values of a number of normal blood samples was carried out. In total, 1585 patient samples were employed to determine the prespecified criterion.

In a preferred embodiment of the inventive method, the method for detecting a dengue infection in a patient blood sample comprises the steps:

a) Performing a valid perox cells analysis comprising determining the number of cells detected passing through a flowcell from a perox channel (valid perox cells);

b) Performing a red blood cells analysis comprising determining a red blood cell count (RBC);

c) Performing a platelet distribution analysis in the sample comprising determining the platelet distribution, its standard deviation and its percentage mean and determining the platelet distribution width by dividing the standard deviation by the percentage mean (PDW);

d) Performing a neutrophil cluster analysis comprising determining the located mean of the neutrophil cluster on the x-axis and determining the located mean of the neutrophil cluster on the y-axis;

e) Performing a raw red cell analysis comprising determining a raw red cell count on a Red Blood Cell (RBC) channel;

f) Determining the percentage of Red Blood Cells (RBCs) with volumes less than 60 fL;

g) Obtaining sample parameters from the values determined in steps a)-f); and h) Evaluating the sample parameters in relation to a prespecified criterion, wherein, if the criterion is fulfilled, a dengue infection is present.

In a preferred embodiment of the inventive method, lower values of the parameters determined in c), and/or lower values of the parameters determined in d) on the y-axis, and/or higher values of the parameters determined in f) are predicative for the presence of a dengue infection.

In a preferred embodiment of the inventive method, values of the parameter determined in a) smaller than 3723.5 cell count and values of the parameter determined in b) larger than $3.77389 \times 10^6$ cells per µL and values of the parameter determined in c) smaller than 64.1605 percent are predicative for the presence of a dengue infection, and/or values of the parameter determined in a) larger than 3723.5 cell count and values of the parameter determined in d) on the x-axis smaller than 63.8149 if scaled to 0 to 99 and values of the parameter determined in e) smaller than 75 cell count and values of the parameter determined in b) larger than $3.94312 \times 10^6$ cells per µL and values of the parameter determined in d) on the y-axis smaller than 78.6959 if scaled to 0 to 99 are predicative for the presence of a dengue infection, and/or values of the parameter determined in a) larger than 3723.5 cell count and values of the parameter determined in d) on the x-axis larger than 63.8149 if scaled to 0 to 99 and values of the parameter determined in f) larger than 29.1512 percent are predicative for the presence of a dengue infection. This has the advantage that the performance of the method is increased to a sensitivity of 90% and a specificity of also 90%.

In another preferred embodiment of the inventive method, the method for detecting a dengue infection in a patient blood comprises the steps:

a) Performing a platelet volumes analysis in the sample and determining the distribution of the platelet volumes;

b) Determining the percentage of Perox cells in the sample with absorption values greater than a predefined limit;

c) Determining the mean value in the Y direction of the Polymorphonucleocyte (PMN) in the sample;

d) Determining the mean platelet concentration in the sample;

e) Obtaining sample parameters from the values determined in steps a)-d); and f) Evaluating the sample parameters in relation to a prespecified criterion, wherein, if the criterion is fulfilled, a dengue infection is present.

In a preferred embodiment of the inventive method, higher values of the parameters determined in d), and/or higher values of the parameters determined in c) are predicative for the presence of a dengue infection.

In a preferred embodiment of the inventive method, values of the parameter determined in a) smaller than $0.758244 \times 10^3$ cells per μL and values of the parameter determined in b) smaller than 0.126523 percent and values of the parameter determined in d) larger than 26.9465 grams per dL are predicative for the presence of a dengue infection and/or values of the parameter determined in a) larger than $0.758244 \times 10^3$ cells per μL and values of the parameter determined in c) larger than 11.2002 are predicative for the presence of a dengue infection. This has the advantage that the performance of the method is increased to a sensitivity of 96% and a specificity of 99%. This means that with full-coverage automated blood examinations the number of false-positive or false-negative diagnosis results could be reduced to a previously unknown extent. This means great progress in respect of a secure dengue infection diagnosis and will lead to a marked improvement of the overall state of health and timely and sensible medical action.

In a preferred embodiment of the inventive method the parameters are determined by scattered light measurement. By contrast with impedance measurement, scattered light measurement involves, as stated above ("optical methods"), a method in which laser light is used, wherein the blood samples (cell by cell) are passed through the laser light and the deflection of the laser beams can be detected by a suitable facility. The method performed using the laser beams is explained in the enclosed FIG. 1. In this method the light beams scattered by the individual cells are detected in various angular ranges (low angle and high angle), which respectively allow information to be obtained about volume (low angle) and density (high angle). In accordance with the invention, an angle of around 2° to 3° deviation from the laser light axis is referred to as a "low angle", an angle of around 5° to 15° as a "high angle". It has transpired that scattered light measurement is superior to impedance measurement in respect of lower susceptibility to errors of the measurement results.

In a preferred embodiment of the inventive method, the dengue infection involves an infection with dengue virus serotype DEN-1, DEN-2, DEN-3 and/or DEN-4.

In a preferred embodiment of the inventive method, the determination of the distribution of the platelet volumes in a) comprises fitting of the platelet volumes to a log-normal distribution.

In a preferred embodiment of the inventive method, the determination of the distribution of the platelet volumes in a) comprises determining the standard deviation of the distribution of the platelet volumes.

Preferably the determination of the distribution of the platelet volumes in a) comprises determining the standard deviation of the log-normal distribution.

In a preferred embodiment of the inventive method, the method is performed by an automated cell counting device.

Another subject of the invention is an automated cell counting device configured to perform the inventive method for detecting a dengue infection in a patient blood sample.

In a preferred embodiment of the automated cell counting device the device comprises at least one scattered light measuring device, at least one flow cytometer, and/or at least one digital holographic microscope.

BRIEF DESCRIPTION OF THE DRAWINGS

Embodiments of the inventive method are also described in greater detail below, which refer to the enclosed figures, in which.

DETAILED DESCRIPTION

First, training data (20) is obtained. Here, patient samples which were positive for any serotype of the dengue virus were obtained from laboratories in India. Data were not subdivided according to serotype as the purpose of this invention is not to discriminate between strains of dengue, but rather to alert to the presence of the virus.

Second, relevant feature vectors (21) from the patient samples are extracted. The samples were measured with an ADVIA 2120i Hematology System from SIEMENS HEALTHINEERS GMBH. The ADVIA 2120i instrument can produce over 400 results. Out of those features, statistical analysis was carried out to determine which features were significantly different between dengue and non-dengue patient samples. The features that showed a significant difference (p<0.05 after correction) were selected to train a classifier.

Third, the classifier is trained to distinguish between positive and negative patient samples based on the selected features. The classification method chosen here was the decision tree for classification. The classification tree model was trained by using a greedy algorithm that splits the dataset based on a feature and calculates how well the resultant split classified the data into positive and negative patient samples. The classification algorithm (22) runs over all features at different split values/combinations and only retains those features which provide the highest predictive capability. Those features that do not provide any additional predictive power are discarded. The classification algorithm (22) used in this case was the standard Classification and Regression Tree predictor-splitting algorithm as implemented in MATLAB.

Figure 5:
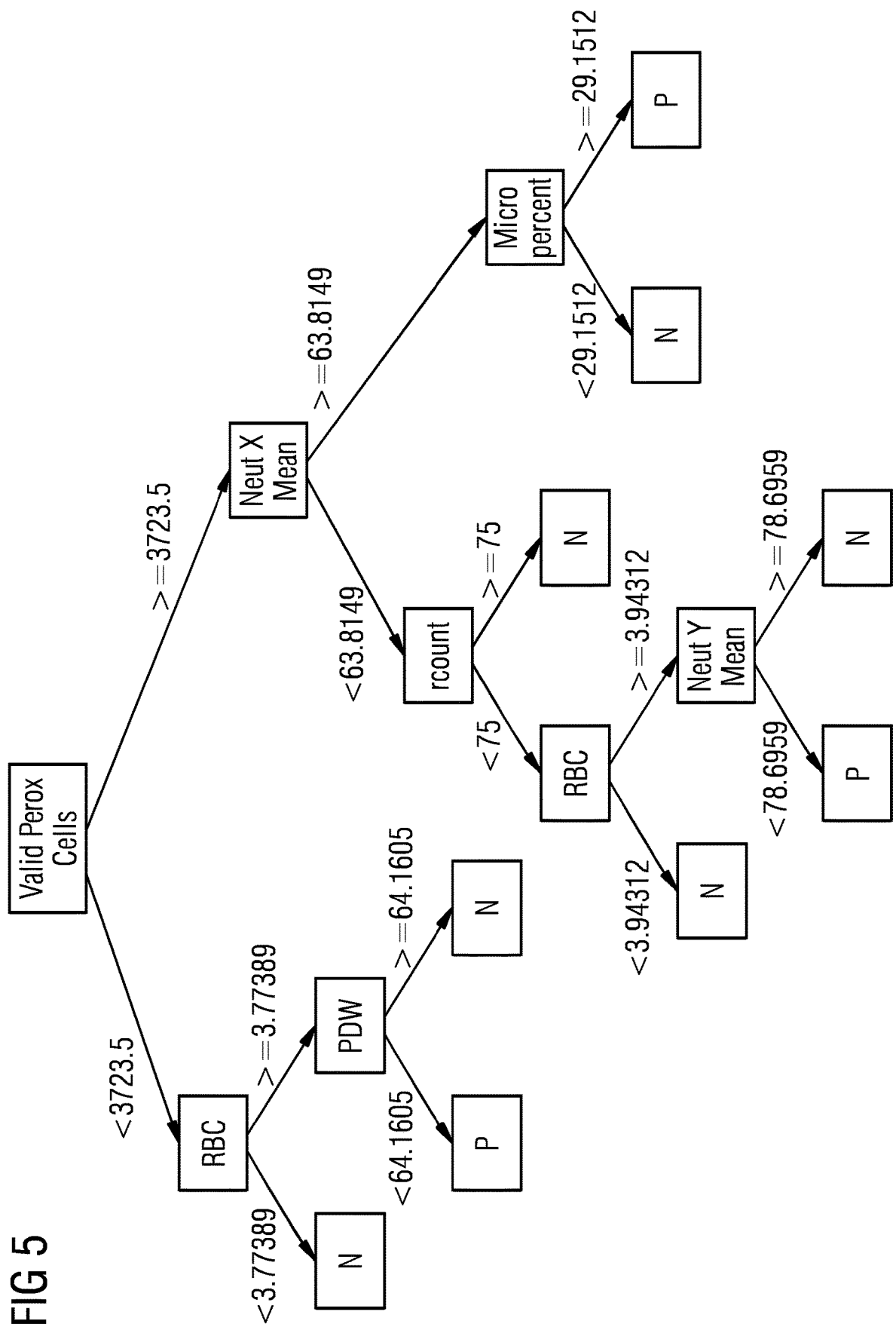
FIG. 5 shows a decision tree representing a hematology parameter and a prespecified criterion according to the invention.
Figure 6:
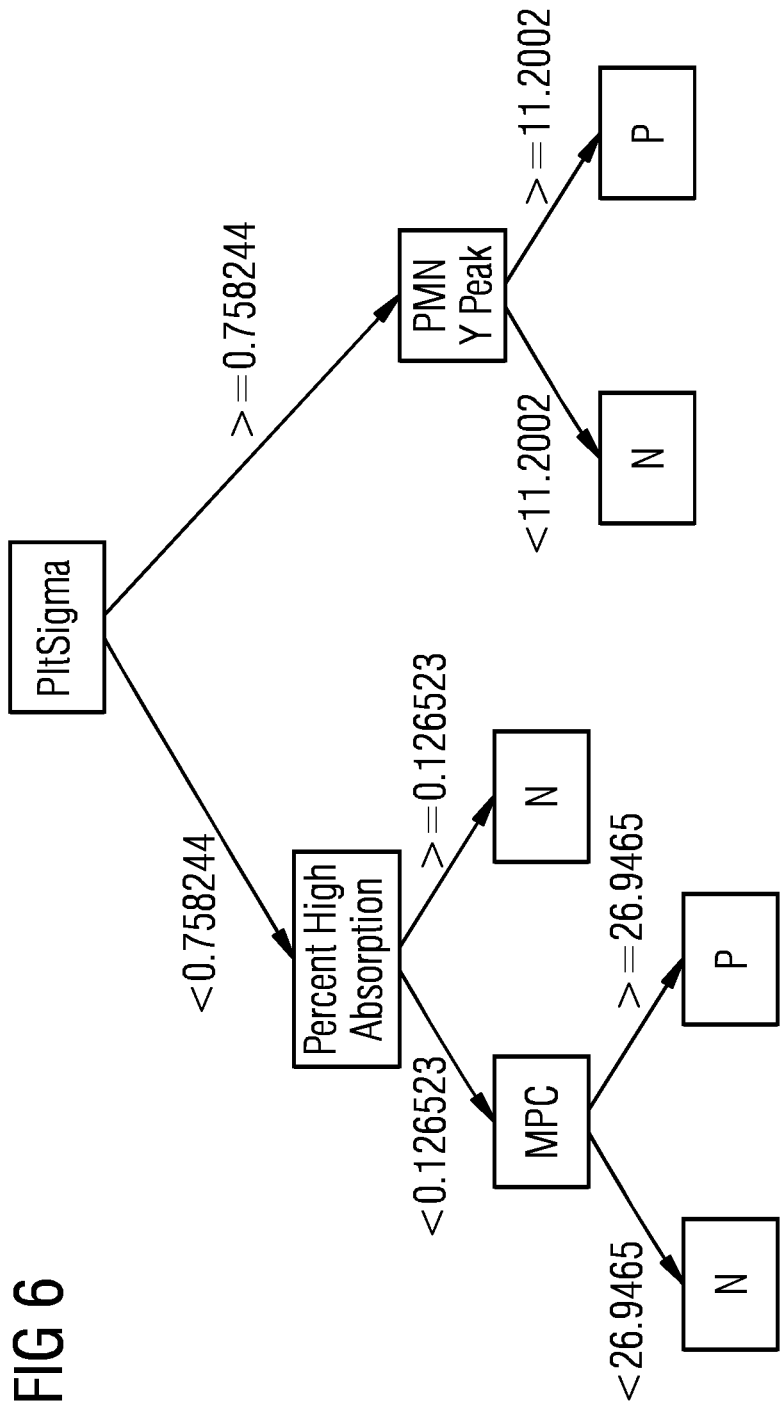
FIG. 6 shows a decision tree representing a hematology parameter and a prespecified criterion according to the invention.

Fourth, the resulting predictive model to diagnose future unknown patients' samples is stored. The predictive model (23) is the algorithm that will ultimately identify those samples that are dengue positive in unknown cases. A visualization of two different models (classification trees to identify dengue positive blood samples) is shown in FIG. 5 and FIG. 6, respectively. The model shown in FIG. 5 is based on such features only which are generally available from Hematology analyzers. The model shown in FIG. 6 uses features generally available from Hematology analyzers as well as features which may not be readily available from Hematology analyzers other than the ADVIA 2120i Hematology System. After training the model on those features described above, the features that ultimately provided the best classification accuracy referring to the model shown in FIG. 5 were those listed in Table 1, and those referring to the model shown in FIG. 6 were those listed in Table 2, below.

TABLE 1

Description of parameters and units.

| Parameter (Feature Name) | Description | Units |
|---|---|---|
| Valid Perox Cells | Number of cells detected passing through the flowcell from the perox channel. | Cell count |
| RBC | The reported Red Blood Cell count. | $10^6$ cells/μL |
| PDW | Platelet distribution width (standard deviation divided by percentage mean). | % |
| Neut X Mean | The located mean of the neutrophil cluster on the x axis. | Scaled to 0-99 |
| Neut Y Mean | The located mean of the neutrophil cluster on the y axis. | Scaled to 0-99 |
| rcount | The raw Red Cell count on a Red Blood Cell channel. | Cell count |
| Micro Percent | Percentage of RBC cells with volume less than 60 fL. | % |

TABLE 2

Description of parameters and units.

| Parameter (Feature Name) | Description | Units |
|---|---|---|
| pltSigma | Platelet volumes are fitted to a log-normal distribution. Platelet Sigma (pltSigma) is the standard deviation of this distribution. | $10^3$ cells/μL |
| Percent High Absorption | Percent High Absorption (Percent_high_absorption) is the percentage of (Perox) cells with absorption values greater than a predefined limit (97). | % |
| PMN Y peak | PMN Y peak (PMN_Y_peak) is the mean value in the Y direction of the Polymorphonucleocyte (PMN) cluster. | Scaled to 0-49 |
| MPC | Mean Platelet Concentration | grams/dL |

Figure 1:
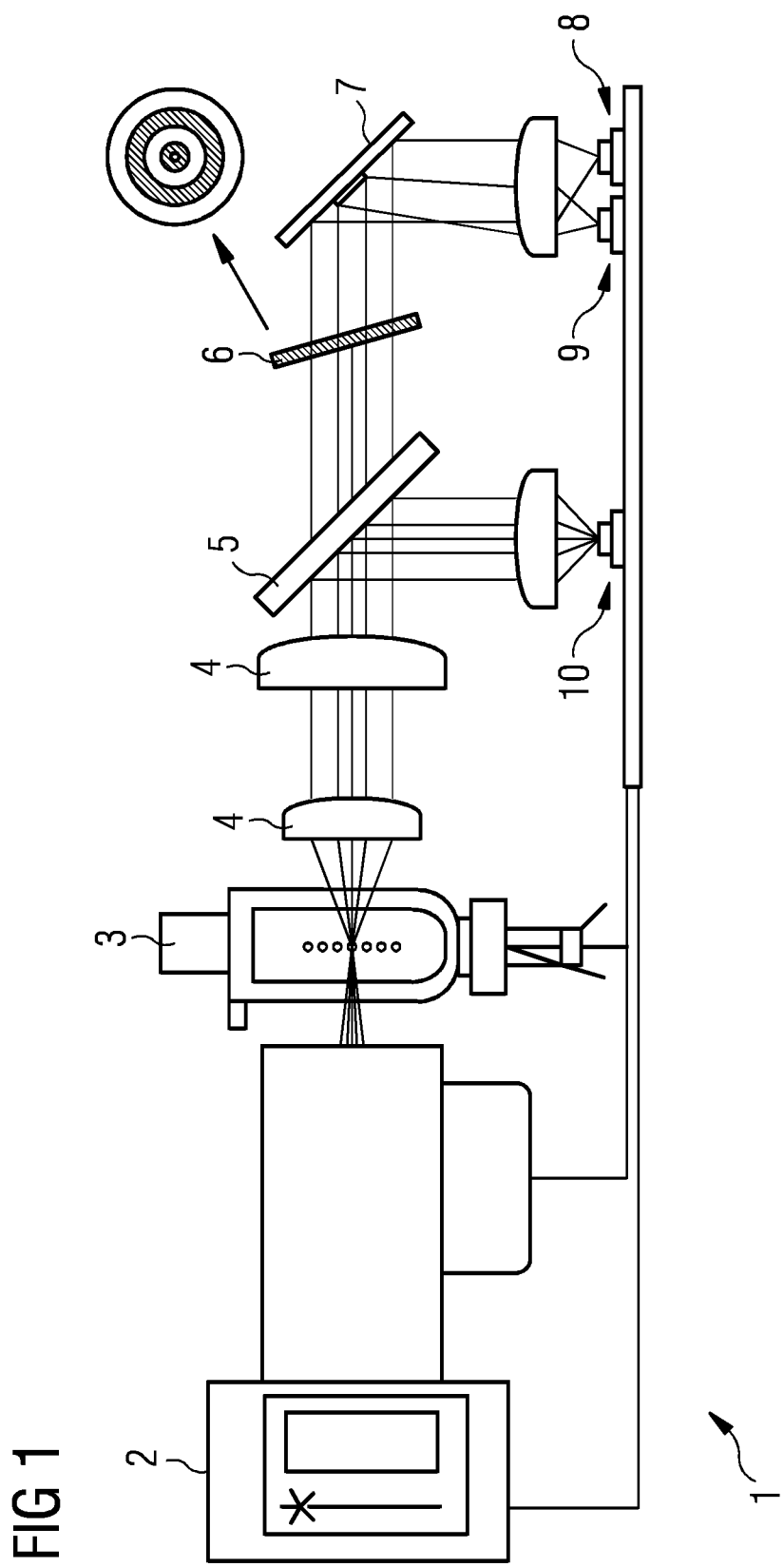
FIG. 1 shows a schematic diagram of a flow cytometry facility 1 for performing the inventive method.
Figure 2:
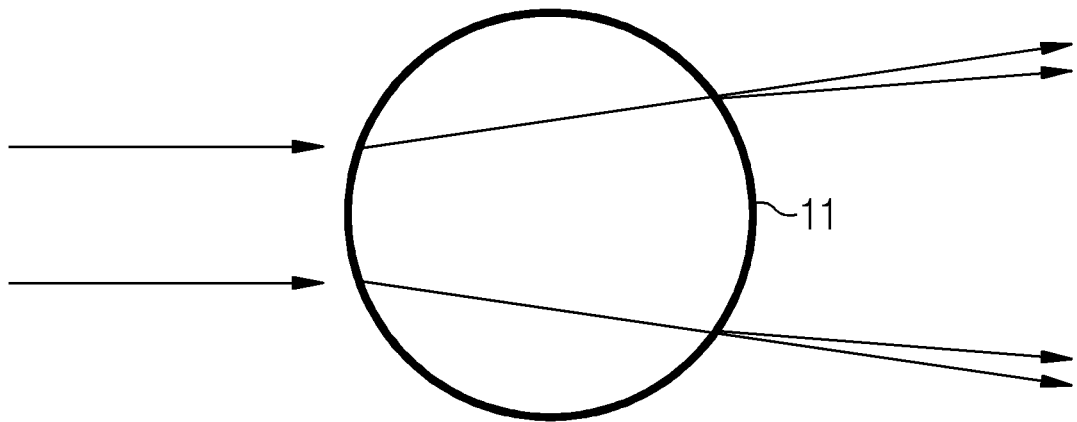
FIG. 2 shows a schematic diagram of the large angle scattered light on the basis of a red blood cell 11, which correlates with the granularity and density of the cell and is measured in a typical range of 5° to 15°. This corresponds to the determination of the cell density.
Figure 3:
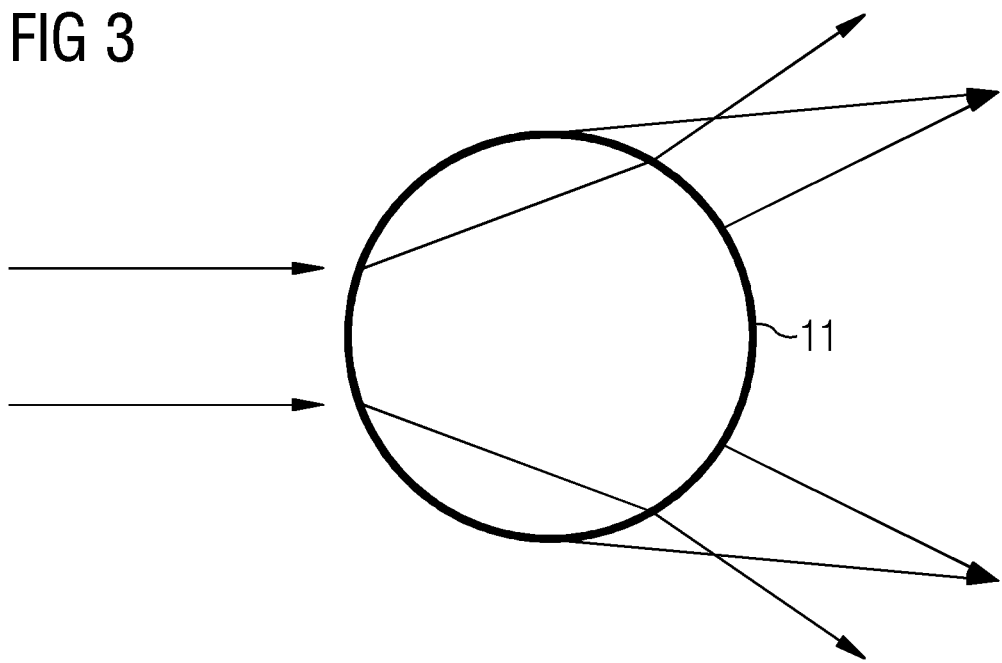
FIG. 3 shows the determination of the cell volume (or of the cell size) of the cell 11 in the low angle scattered light range (2° to 3°).
Figure 4:
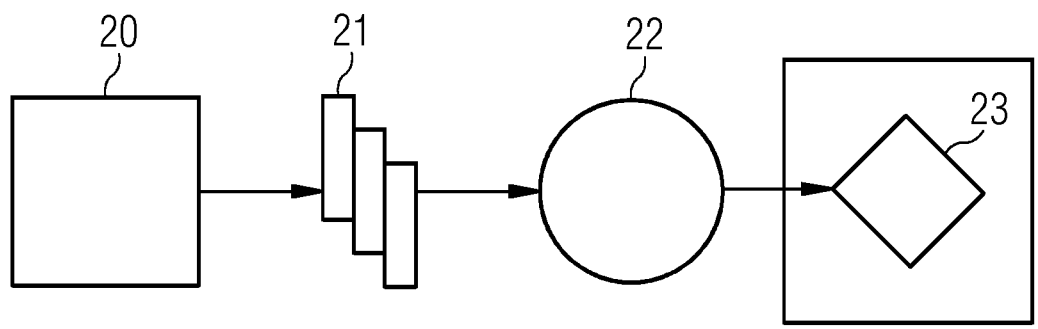
FIG. 4 shows a process by which a prespecified criterion is determined which is used for evaluating sample parameters in a method for detecting a dengue infection in a patient blood sample according to the invention.

The ADVIA 2120 produces a cytogram based on essentially how much a cell scatters light. Every cell has a scatter high value (the low angle scattered light, see, e.g., FIG. 3) and a scatter low value (the large angle scattered light, see, e.g. FIG. 2) which comes from how much light (intensity) hits the high or low detector on a scale of 0 to 49. The scatter high and low are then plotted as a scatter diagram (cytogram) with high on the x-axis, low on the y-axis. The PMN Y peak is the peak of the PMN cluster of cells in the Y direction.

The models generated to identify dengue virus are as follows: Each node in the decision trees shown in FIGS. 5 and 6 represents a hematology parameter (see Table 1 and Table 2, respectively) and the respective prespecified criterion. The terminating branches decide whether the new sample will be classified as dengue positive (P) or negative (N) depending on the corresponding measured parameter value of the sample to be classified.

These models were trained on a set of 1585 patient samples. In order to prevent overfitting, cross validation was carried out by partitioning the data into 5 sets, 4 of which were used to train the model and 1 used to validate. This was carried out 5 times for each subset to test the model and the results averaged. Ten percent (10%) of the data was also held out of the analysis entirely, in order to judge the resulting model on data it had never seen before.

The performance of the models yielded a sensitivity of 90% and a specificity of 90% (model shown in FIG. 5) and a sensitivity of 96% and a specificity of 99% (model shown in FIG. 6), respectively. A combination of the two models can additionally be of advantage.

The inventive method enables on the basis of the prespecified criterions as determined above, the evaluation of the determined parameters, and a prediction of a dengue infection with high specificity and sensitivity using standard Hematology Systems.

LIST OF REFERENCE CHARACTERS

1 Facility for flow cytometry
2 Laser
3 Sensor module
4 Optical lenses
5 Semi-transparent mirror
6 Aperture
7 Mirror
8 Sensor
9 Sensor
10 Sensor
11 Cell
20 Training data
21 Feature vectors
22 Classification algorithm
23 Model
P Positive
N Negative

The invention claimed is:

1. A method for detecting a dengue infection in a patient blood sample, comprising the steps of:
   a) performing a platelet volumes analysis in the sample and determining a distribution of the platelet volumes;
   b) determining a percentage of Perox cells in the sample with absorption values greater than a predefined limit;
   c) determining a mean value in a Y direction in a scatter diagram of a Polymorphonucleocyte (PMN) in the sample;
   d) determininge a mean platelet concentration (MPC) in the sample;
   e) obtaining sample parameters from values determined in steps a)-d); and
   f) evaluating the sample parameters in relation to a prespecified criterion, wherein, if the criterion is fulfilled, a dengue infection is present.

2. The method as claimed in claim 1, wherein higher values of parameters determined in d) of claim 1, or higher values of parameters determined in c) of claim 1 are predicative for the presence of a dengue infection.

3. The method as claimed in claim 1, wherein:
   values of a parameter determined in a) of claim 1 smaller than $0.758244 \times 10^3$ cells per μL and values of a parameter determined in b) of claim 1 smaller than 0.126523 percent and values of a parameter determined in d) of claim 1 larger than 26.9465 grams per dL are predicative for the presence of a dengue infection or
   values of the parameter determined in a) of claim 1 larger than $0.758244 \times 10^3$ cells per μL and values of a parameter determined in c) of claim 1 larger than 11.2002 are predicative for the presence of a dengue infection.

4. The method as claimed in claim 1, wherein the sample parameters are determined by scattered light measurements.

5. The method as claimed in claim 1, wherein the dengue infection involves an infection with dengue virus serotype DEN-1, DEN-2, DEN-3 or DEN-4.

6. The method as claimed in claim 1, wherein the determination of the distribution of the platelet volumes in a) of claim 1 comprises fitting of the platelet volumes to a log-normal distribution.

7. The method as claimed in claim 1, wherein the determination of the distribution of the platelet volumes in a) of claim 1 comprises determining the standard deviation of the distribution of the platelet volumes.

8. The method as claimed in claim 1, wherein the determination of the distribution of the platelet volumes in a) of claim 1 comprises determining the standard deviation of the log-normal distribution.

* * * * *